United States Patent [19]

Sawada et al.

[11] Patent Number: 5,213,980
[45] Date of Patent: May 25, 1993

[54] FIBROBLAST GROWTH FACTOR GENE TRANSFORMED HYBRIDOMA AND ENHANCED PRODUCTION OF ANTIBODY

[75] Inventors: Hidekazu Sawada, Osaka; Keiji Iwamoto, Hyogo; Kazuaki Kitano, Osaka, all of Japan

[73] Assignee: Takeda Chemical Industries, Ltd., Osaka, Japan

[21] Appl. No.: 706,946

[22] Filed: May 29, 1991

[30] Foreign Application Priority Data

Jun. 1, 1990 [JP] Japan .................. 2-145180

[51] Int. Cl.$^5$ .............................. C12N 5/12
[52] U.S. Cl. .................. 435/240.27; 435/172.3; 435/69.1; 435/69.4; 935/55
[58] Field of Search ............ 435/240.27, 172.3, 69.1, 435/69.4; 935/55

[56] References Cited

FOREIGN PATENT DOCUMENTS 0307247 3/1989 European Pat. Off. .

OTHER PUBLICATIONS

Kovar, J. "Hybridoma Cultivation in Defined Serum--Free Media: Growth Supporting Substances..." Folia Biologica (Praha) 32:304-310, 1986.

Pendse & Bailey, "Effects of Growth Factors on Cell Proliferation And Monoclonal Antibody Production of Batch Hybridoma Cultures", Biotechnology Letters, vol. 12, No. 7, 487-492 (1990).

Sasada et al. Molecular & Cellular Biology 8 588 (1988).

Harlow et al. from Antibodies, A Laboratory Manual, Cold Spring Harbor, pp. 142, 241, 245-253, 1988.

Gospodarowicz, D. Nature, 249:123 (1974).

Genot, et al. Cellular Immunology, 122:424 (1989).

Sasada, et al. Molecular and Cellular Biology, 8:588 (1988).

Primary Examiner—Robert J. Hill, Jr.
Assistant Examiner—Nina Ossanna
Attorney, Agent, or Firm—David G. Conlin; Gregory D. Williams

[57] ABSTRACT

Disclosed are (1) a hybridoma carrying a vector for expressing a fibroblast growth factor (FGF) protein gene; (2) a method for producing the hybridoma of (1) which comprises transforming a hybridoma with the vector for expressing the FGF protein gene; and (3) a method for producing a biologically active substance which comprises cultivating in a culture medium the hybridoma obtained by the method of (2) using a hybridoma producing a biologically active substance other than the FGF protein, producing the FGF protein and producing and accumulating the biologically active substance in a culture, and recovering the biologically active substance, whereby the biologically active substance can be efficiently produced and recovered using the serum-free medium, which is advantageous for industrial production and very useful for an improvement in the breeding of the hybridoma.

6 Claims, 1 Drawing Sheet

FIBROBLAST GROWTH FACTOR GENE TRANSFORMED HYBRIDOMA AND ENHANCED PRODUCTION OF ANTIBODY

TECHNICAL FIELD

The present invention relates to a method producing improved hybridomas by introducing FGF protein genes into the hybridomas, wherein the hybridoma comprises a lymphocyte as one parent cell. More particularly, the present invention relates to a technique for facilitating the cloning and/or the cultivation of hybridomas in serum-free culture media and for producing desired products from the hybridomas stably and efficiently by introducing FGF protein genes into the hybridomas and by expressing FGF proteins in the culture (in cells or media).

BACKGROUND ART

There is a continuing need to cultivate lymphoid cells which produce useful biologically active substances such as lymphokines (for example, interferons and interleukins) and monoclonal antibodies (hereinafter also briefly referred to as MoAbs). For the cultivation of lymphoid cell strains, culture media containing about 10% of sera are mainly used as with other cells. In particular, fetal calf serum (FCS)-containing culture media have usually been employed. Serum-free culture media has also been employed, but such media are generally poor in cell proliferation, particularly when compared to the serum-containing culture media. For this reason, it is necessary to increase the seeding density on cell passage when serum-free media is employed. In order to improve proliferation in serum-free culture media, some groups have attempted to obtain cell strains improved in proliferative activity by the method of cell-adaptation to the serum-free culture media or the method of inducing mutations. However, with respect to lymphoid cell lines such as hybridomas, there has been no improvement in the proliferative activity by using recombinant technology.

In recent years, various factors have been isolated and their genes have been elucidated with the advance of investigations on cell growth factors. Fibroblast growth factors (FGFs), one kind of the above-mentioned cell growth factors, are cell growth factors discovered from the bovine pituitary glands by D. Gospodarowicz [*Nature* 249, 123 (1974)]. There are two types of FGF, basic FGF (bFGF) which is basic in its isoelectric point and acidic FGF (aFGF) which is acidic in its isoelectric point. The amino acid sequences of both bFGF and aFGF have been elucidated [Bovine bFGF: Proc. Natl. Acad. Sci. USA 82, 6507-6511 (1985); Human bFGF: The EMBO Journal 5, 2523-2528 (1986); Human and bovine bFGF: Biochem. Biophys. Res. Commun. 138, 611-617 (1986)]. FGFs are cell growth factors exhibiting proliferation promoting activity in almost all mesoderm-derived cells such as adrenal cell Y1 [*Endocrinology* 97, 120 (1975], myoblasts [*J. Cell Biol.* 70, 395 (1976)], chondrocytes [*J. Cell. Physiol.* 91, 977 (1977)]and vascular endothelial cells [*Proc. Natl. Acad. Sci. U.S.A.* 73, 4120 (1976)], as well as to fibroblasts [*J. Cell Biol.* 66, 451 (1975)]. However, it is known that FGFs do not generally exhibit proliferation promoting activity in epithelial cells [*Saibo Seicho Inshi* (Growth Factors), page 32, edited by The Japanese Tissue Culture Association, Asakura Shoten, 1984]. The present inventors have discovered that biologically active substances can be efficiently produced from lymphoid cells such as hybridomas by cultivating the lymphoid cells in FGF- containing culture media. And there is a report that FGFs increase the proliferative response of B cells activated by mitogen to low molecular weight B cell growth factor [*Cellular Immunology* 122, 424 (1989)]. However, until the present invention, introduction of FGF gene into lymphoid cells to improve the proliferative activity of Cells has not been reported at all.

As noted above, the aminoacid and nucleotide sequences of both aFGF and bFGF have already been determined, which sequences reveal that both FGFs are synthesized at first as peptides each having 155 amino acid residues and that no signal peptide sequences for secretion are observed in their nucleotide sequences [J. A. Abraham et al., *Science* 233, 545-548 (1986); and M. Jaye et al., *Science* 233, 541-545 (1986)].

When useful substances are produced by cultivating animal cells, various problems are pointed out about the use of the serum culture media. Namely, the sera vary in quality among lots, and have the danger of infection with mycoplasma and viruses. Further, there is a fear of exerting adverse effects on the quality of the products produced because of the complicated purification process.

The serum-free culture media is therefore advantageously used, but is generally found to be poor in cell proliferation. For this reason, the productivity of such useful substances is diminished in many cases. Under such conditions, where there is poor cell proliferation, the cells are typically required to be inoculated at a high cell density (for example, in the serum-free culture of human-human hybridomas producing human MoAbs, a cell density of about $1 \times 10^5$ cells/ml is necessary). In large-scale cultivation on an industrial scale, therefore, the complexity of increased cell passage cycles arises, and the danger of contamination with mycoplasma and viruses is also increased. Further, no techniques for cloning cells by limiting dilution culture methods using serum-free culture media have been established yet.

The present inventors considered that such problems could be solved if a mutant strain exhibiting high proliferative activity, even in serum-free culture media, could be obtained. Several attempts were made to improve the cells proliferative activity by conventional methods such as mutations. However, satisfactory results were not obtained. Even if a desired mutant strain is obtained, that method is time-consuming and cannot be said to be a sure method.

In recent years, expression vectors using animal cells as host cells have been developed. The present invention was completed by improving proliferative activity of hybridomas using genetic engineering techniques, thus solving the above-mentioned problems.

DISCLOSURE OF INVENTION

Figure 1:
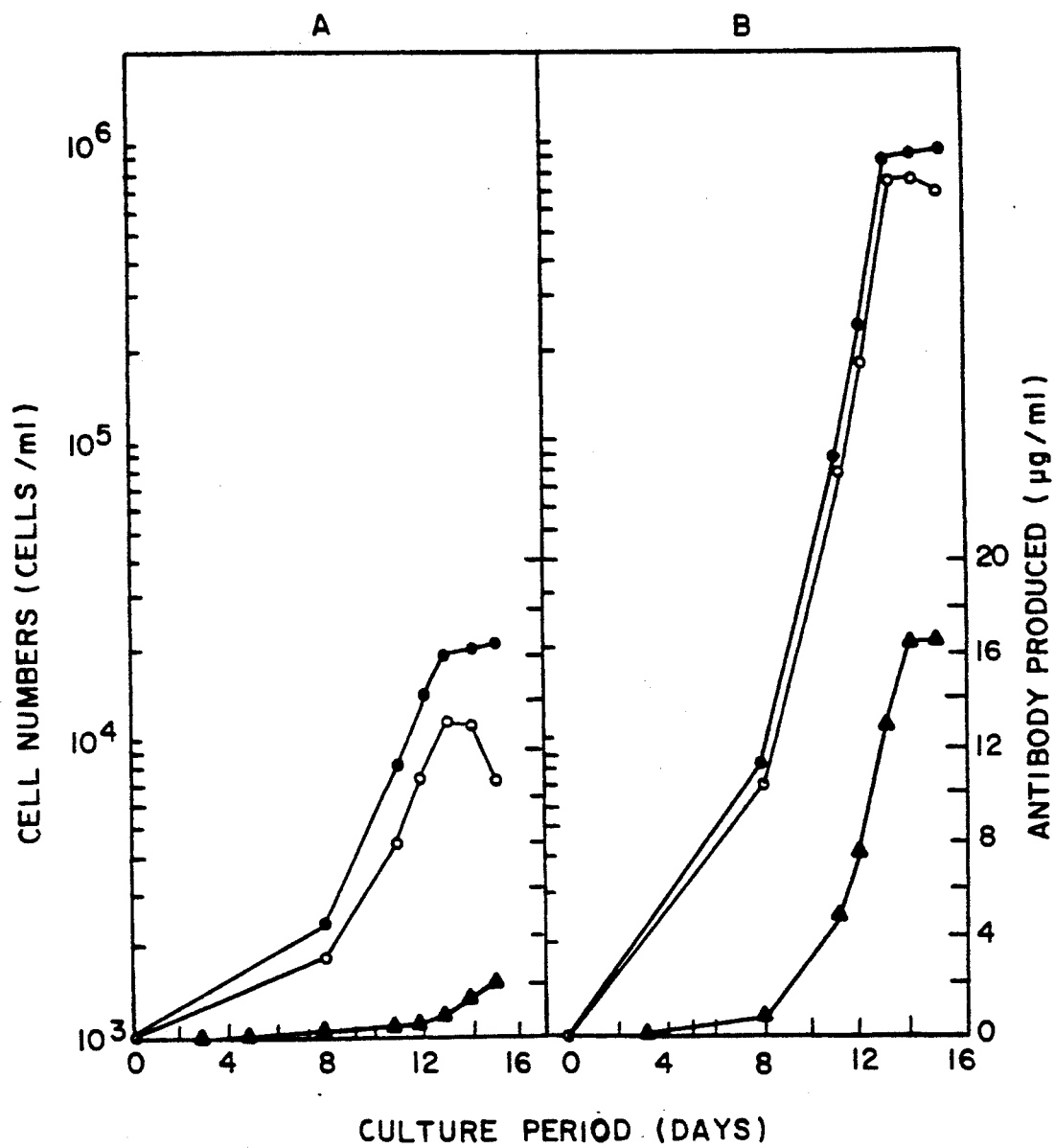
FIGS. 1 (A and B) shows the time course of an agitation culture of a bFGF gene-free original cell line (FIG. 1(A)) and a bFGF gene transfected cell line (FIG. 1(B)) at a low cell density (refer to Example 4).

The present inventors have diligently studied and established a method for cultivating cells from a single hybridoma cell or a low cell density, using serum-free culture media. More specifically, the present inventors have discovered that cell proliferation potency is significantly improved by introducing FGF genes into the cells.

In accordance with the present invention, there is provided (1) a hybridoma carrying a vector for expressing a fibroblast growth factor (FGF) protein gene, (2) a method for producing the hybridoma of the above item (1), which comprises transfecting a hybridoma with the vector for expressing the FGF protein gene, and (3) a method for producing a biologically active substance, which comprises cultivating in a culture medium the hybridoma obtained by the method of the above item (2) using a hybridoma producing a biologically active substance other than a FGF protein, producing the FGF protein and accumulating the biologically active substance in a culture, and recovering the biologically active substance.

BEST MODE FOR CARRYING OUT THE INVENTION

In the present invention, any FGF protein may be used as long as it is a polypeptide or a protein having FGF activity. Further, as the FGF protein, either bFGF protein, which is basic in its isoelectric point, or aFGF which is acidic in its isoelectric point may be used.

Furthermore, the FGF proteins may contain FGFs which are known to be obtained by recombinant DNA technology [PCT International Publication No. WO/87/01728; *FEBS Letters* 213, 189 (1987); and EP Publication No. 237,966 (Japanese Patent Unexamined Publication No. 63-226287/1988)]and FGF muteins [EP Publication No. 281,822 (Japanese Patent Unexamined Publication No. 2-193/1990); *Biochemical and Biophysical Research Communications* 151, 701 (1988); and EP Publication No. 326,907]the disclosures of which are hereby incorporated by reference.

The above-mentioned FGF muteins are obtained essentially by variations of the amino acid sequences of the original peptides or proteins. Such variations include addition of amino acid residue(s), deletion of constituent amino acid residue(s) and/or substitution of constituent amino acid residue(s) by different amino acid residue(s).

Such addition of amino acid residue(s) includes addition of at least one amino acid residue.

Such deletion of constituent amino acid residue(s) includes deletion of at least one FGF-constituent amino acid residue.

Such substitution of constituent amino acid residue(s) by different amino acid residue(s) includes substitution of at least one FGF-constituent amino acid residue by at least one different amino acid residue.

At least one amino acid residue in the mutein which has at least on amino acid residue added to the FGF excludes methionine derived from an initiation codon used for peptide expression and a signal peptide.

The number of the added amino acid residue(s) is at least on.. However, it may be any number as long as FGF characteristics are not lost. More preferably, some or all of the amino acid sequences of proteins which have homology with the FGFs and which exhibit activity similar to that of the FGFs are included.

As to the number of the deleted FGF-constituent amino acid residue(s) in the mutein which lacks at least one FGF-constituent amino acid residue, it may be any number as long as FGF characteristics are not lost.

Examples of the deleted constituent amino acid residues include (1) the 10 residues on the amino terminal side of human bFGF, from Met$^1$ to Ser$^{10}$;
(2) the 14 residues on the amino terminal side of human bFGF, from Met$^1$ to Pro$^{14}$;
(3) the 41 residues on the amino terminal side of human bFGF, from Met$^1$ to Val$^{41}$; and
(4) the 61 residues on the carboxyl terminal side of human bFGF, from Lys$^{87}$ to Ser$^{147}$.

The FGF muteins further include muteins lacking the 7 to 46 constituent amino acid residues on the carboxyl-terminal side of the original peptide or protein of bFGF.

As for the number of at least one FGF-constituent amino acid residue prior to substitution in the FGF mutein in which at least one FGF-constituent amino acid residue is substituted by at least one different amino acid residue, it may be any number as long as FGF characteristics are not lost.

Examples of the constituent amino acids prior to substitution include cysteine and cystine, but cysteine is preferable. The constituent amino acids other than cysteine prior to substitution include aspartic acid, arginine, glycine, serine and valine.

When the constituent amino acid prior to substitution is cysteine, for example, neutral amino acids are preferable as the substituted amino acids. Specific examples of such neutral amino acids include glycine, valine, alanine, leucine, isoleucine, tyrosine, phenylalanine, histidine, tryptophan, serine, threonine and methionine. Serine and threonine are particularly preferred.

When the constituent amino acid prior to substitution is any one other than cysteine, amino acids which are different, for example, in hydrophilicity, hydrophobicity or electric charge from the amino acid prior to substitution are selected as the substituting different amino acids. Specifically, when the amino acid prior to substitution is aspartic acid, the substituting amino acids include asparagine, threonine, valine, phenylalanine and arginine. In particular, asparagine and arginine are preferable.

When the amino acid prior to substitution is arginine, the substituting amino acids include glutamine, threonine, leucine, phenylalanine and aspartic acid. Glutamine is especially preferable.

When the constituent amino acid prior to substitution is glycine, the substituting amino acids include threonine, leucine, phenylalanine, serine, glutamic acid and arginine. Threonine is particularly preferred.

When the constituent amino acid prior to substitution is serine, the substituting amino acids include methionine, alanine, leucine, cysteine, glutamine, arginine and aspartic acid. In particular, methionine is preferable.

When the constituent amino acid prior to substitution is valine, the substituting amino acids include serine, leucine, proline, glycine, lysine and aspartic acid. Serine is especially preferred.

As the substituting amino acids, asparagine, glutamine, arginine, threonine, methionine, serine and leucine are preferably selected.

The most preferred substituted muteins include a mutein in which cysteine, the constituent amino acid, is substituted by serine.

In the above substitution, the substitution of at least two constituent amino acids may be simultaneously carried out. In particular, it is preferred that two or three constituent amino acids are substituted.

The FGF muteins may be obtained by a combination of two or three of the above-mentioned addition, deletion and substitution.

As the FGF mutein, a mutein is preferable in which at least one human bFGF-constituent amino acid residue is substituted by at least one different amino acid residue.

Any FGF protein gene may be used in the present invention as long as it codes for the above-mentioned proteins. For example, such FGF protein genes can be obtained from the cells of the brains, the retinas, the kidneys and the prostates of mammals such as humans, monkeys, rabbits, sheep, bovines, chickens, dogs, pigs and mice, or from various FGF protein-producing transformant cells. The FGF protein genes can be obtained by methods known in the art, for example, by using the cloning technique of extracting messenger RNA (mRNA) from the above-mentioned cells, preparing its complementary DNA (cDNA) enzymatically, binding a suitable vector thereto followed by proliferation in host cells such as *E. coli*, and selecting a single colony having the vector into which the FGF protein gene is incorporated. Further, various commercially available cDNA libraries may also be used such as bovine brain cDNA, bovine retina cDNA, chicken brain cDNA, dog kidney cDNA and human brain cDNA. Furthermore, the amino acid sequences of bovine or human bFGF and aFGF and the nucleotide sequences of their genes have already been published [T. Kurokawa et al., *FEBS Letters* 213, 189–194 (1987); and F. Esch et al., *Biochem. Biophys. Res. Commun.* 133, 554–562 (1985)]. Based thereon, therefore, oligonucleotides having appropriate nucleotide sequences may be prepared by organic synthesis according to methods known in the art, and can be used as probes for colony selection in the above-mentioned cloning. Additionally, the FGF protein genes can be prepared from vectors (for example, plasmids) into which the FGF protein genes are incorporated, or from transformant cells carrying the vectors. The FGF protein genes can further be prepared by chemical synthesis, based on the known amino acid sequences of aFGF and bFGF or the muteins thereof, or based on the nucleotide sequences of the genes thereof. In the present invention, not only the genes coding for bFGF or aFGF, but also mutant genes thereof (for example, genes coding for FGF muteins) can be used as the FGF protein genes as long as FGF activity is not lost when the genes are expressed as the FGF proteins.

The FGF protein genes are introduced into the hybridomas in the constitutively or inductively expressible state. For this purpose, it is preferable to introduce the appropriate vector for expressing the FGF protein gene (hereinafter also briefly referred to as "expression vector") into the hybridoma to transform it. The expression vector is incorporated with a DNA sequence in which a constitutively or inductively operable promoter, a translation initiating codon (ATG) and the FGF protein gene are arranged in this order.

Examples of vectors used for the expression vectors include but are not limited to pSVL [*Mol. Cell. Biol.* 4, 817 (1984)], pCH 110 [*J. Mol. App. Genet.* 2, 101 (1983); and *Cell* 39, 653 (1984)], pKSV-10 [*Cell* 23, 175 (1981)], pSV2 [*Proc. Natl. Acad. Sci., U.S.A.* 78, 2072 (1981)]. pBTV$_{69T}$ [*Methods in Enzymol.* 101, 387 (1983)], pHEBo [*Mol. Cell. Biol.* 5, 410 (1985)], pZIP-NeoSV [*Cell.* 37, 1053 (1984)]and pMAM$_{neo}$ [*Nature* 294, 228 (1981)]the disclosures of which are hereby incorporated by reference.

Any promoter may be incorporated upstream from the above-mentioned translation initiating codon as long as it is suitable for the hybridoma used for expression of the FGF protein gene. Examples of such promoters include the promoter of a metallothionein gene [D. H. Hamer, *Ann. Rev. Biochem.* 55, 913 (1986)], and promoters existing in the promoter region of SV (simian virus) 40 [Okayama et al., *Mol. Cell. Biol.* 3, 280-289 (1983)]and various retrovirus LTR (long terminal repeat) regions the disclosures of which are hereby incorporated by reference.

Examples of retrovirus LTR region-derived promoters include Abelson murine leukemia virus (A-MuLV) [S. P. Goff et al., *Cell* 22, 777–785 (1980)], Moloney mouse leukemia virus (M-MuLV) [Niwa et al., *Cell* 32, 1105–1113 (1983)], adult T cell leukemia virus (ATLV) [Yoshida et al., *Proc. Natl. Acad. Sci. U.S.A.* 79, 6899–6902 (1982)]. and avian sarcoma virus (ASV) [Kitamura et al., *Nature* 297, 205–208 (1982)] the disclosures of which are hereby incorporated by reference.

The promoter of the metallothionein gene is also constitutively expressed, but the expression is induced more strongly by heavy metals such as Cd, Zn, Hg, Ag, Cu and Au.

In the present invention, one or more of the above-mentioned promoters may be used.

Further, upstream from the 5'-terminus of the FGF protein gene, the above-mentioned expression vector may have a nucleotide sequence coding for, for example, the signal peptide consisting of the -21st to -1st codons shown in FIG. 2 of Japanese Patent Unexamined Publication No. 61-52293/1986 the disclosure of which is hereby incorporated by reference.

Furthermore, the above-mentioned expression vector may have TAA, TGA or TAG as a translation terminating codon at the 3'-terminus of the FGF protein gene. In particular, TAG is preferable.

The expression vectors used for transfection of the hybridomas may further have enhancers. Such enhancers include virus-derived enhancers such as enhancers existing in the SV40 promoter region (Okayama et al., previously described) or in the retrovirus LTR region. In particular, the enhancer of the nucleotide sequence repeating portion in the above-mentioned LTR region is preferably used.

Examples of the retrovirus-derived enhancers include A-MuLV (S. P. Goff et al., previously described), M-MuLV (Niwa et al., previously described), ATLV (Yoshida et al., previously described) and ASV (Kitamura et al., previously described).

In the present invention, one or more of the above-mentioned enhancers may be used.

In introducing the FGF protein gene into the hybridoma, namely in transfecting the hybridoma, the FGF protein gene is typically placed together with a drug-resistant gene such as neomycin-resistant gene on the same expression vector, followed by introduction into the hybridoma or co-transformation [*Cell* 16, 777 (1979)], whereby a desired transformant can be easily selected.

In co-transformation, a plasmid bearing gene (A) which is a mark for selection of the transformant (for example, antibiotic-inactivating genes such as ampicillin-resistant, neomycin-resistant or hygromycin-resistant genes) and a plasmid bearing FGF protein gene (B) to be introduced are simultaneously introduced into a cell by an electroporation method or the like, wherein the plasmid bearing gene (B) is used in a larger amount than the plasmid bearing gene (A). When cultivation is conducted in the presence of drug to which the cells having gene (A) is resistant and proliferated clones are selected, cell lines having both of genes (A) and (B) can be obtained.

Examples of the hybridoma cell lines used in the present invention include mouse hybridoma, mouse human-human heterohybridoma and human-human hybridoma, wherein one parent cell of said hybridomas is a lymphoid cell. More specific examples thereof include mouse hybridoma E235I63 [*Hybridoma* 4, 47 (1985), mouse human-human heterohybridoma I12-22.25 [*Biochem. Biophys. Res. Commun.* 129, 26 (1985)], human-human hybridoma W471-7.24 [*Biochem. Biophys. Res. Commun.* 142, 805 (1987)], HBW-4.16, HBW-6.20 [*Bio/Technoloqy* 7, 374 (1989)]and hybridomas derived therefrom the disclosures of which are hereby incorporated by reference. In particular, monoclonal antibody-producing hybridomas are preferable, and more particularly human monoclonal antibody-producing human-human hybridoma is preferably used.

As the culture media used to cultivate the hybridomas, conventional serum-containing culture media, serum substitute-containing culture media or serum-free culture media can be employed. The serum-containing culture media include 10% fetal calf serum-containing culture media, and the serum substitute-containing culture media include culture media to which about 3 mg/ml of a serum-derived growth promoting factor fraction (GFS) [*Text for 2nd Symposium on Research and Development Protect of Basic Technoloqy for Future Industries-Biotechnoloqy* 1, 61 (1984) is added. As the culture media for producing useful biologically active substances such as monoclonal antibodies, however, the serum-free culture media are desirable and preferred because of easy purification and inexpensive cost of the media. As the serum-free culture media, media prepared by adding factors such as insulin, transferrin, ethanolamine, selenium and polyethylene glycol to basal synthetic media are used. The basal synthetic media include Iscove's medium [N. N. Iscove & F. Melchers, *J. Exp. Med.* 147, 923 (1978)], Ham F12 medium [R. G. Ham, *Proc. Natl. Acad. Sci.* 53, 288 (1965)], L15 medium [A. Leibovitz, *Amer. J. Hyg.* 78, 173 (1963)], T medium (Japanese Patent Unexamined Publication No. 60-145088/1985) and TL-2 medium (the 1:1:2 mixture of Iscove's medium, Ham F12 medium and L15 medium). In particular, T medium or TL-2 medium is preferably used.

For cultivation of the hybridomas, vessels or devices usually employed for cultivation are appropriately used. Such vessels or devices include multiwell plates, tissue culture flasks, spinner flasks, jar fermentors, large-scale fermentors, hollow fiber reactors and ceramic matrix reactors. Cultivation methods using microcapsule may also be employed.

In the present invention, cultivation is conducted under conditions suitable for cultivation of the hybridomas to be used. In general, cultivation is carried out at a cultivating temperature of about 37° C. at a pH of about 6.5 to 7.5 for several days to 3 months. For example, when 0.1 to $5 \times 10^5$ cells/ml of cells are inoculated in the culture medium used in the present invention on a multiwell plate or in a flask, cultivation is conducted in a 5% carbon dioxide incubator (an incubator containing carbon dioxide of a concentration of 5%) at about 37° C. at pH of about 6.5 to 7.5 for about 1 to 20 days. When jar fermentors or large-scale fermentors are used, aeration-agitation culture is carried out. Further, in cultivation by these fermentors, hollow fiber reactors and ceramic matrix reactors and in cultivation using microcapsules, the productivity of the biologically active substances can be increased by exchanging the media in a batch or continuous manner. Continuous perfusion culture is continued for 1 to several months (about 3 months) in some cases. Aeration is carried out if necessary.

In order to recover the cells from the culture broth, the culture broth is directly subjected to a centrifuge or a filter. Biologically active substances other than the FGF protein, which are produced by cultivation of the hybridomas, are recovered from a supernatant obtained by filtration or centrifugation, when the substances are accumulated in the culture supernatant. When the substances are accumulated in the cells, the cells obtained by filtration or centrifugation are treated by physical methods (for example, ultrasonic oscillation, French press and Dyno-Mill) or chemical methods (for example, guanidine hydrochloride) to extract the products, thereby obtaining a supernatant.

The biologically active substances can be separated from the above-mentioned supernatant and purified by appropriate combinations of conventional separating and purifying methods. For example, when the biologically active substances are proteins or peptides, such methods include methods utilizing a difference in solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse-phase high performance liquid chromatography and methods utilizing a difference in isoelectric point such as isoelectric point electrophoresis.

Hybridomas can be cultivated in serum-free media even under low inoculum density by introducing the FGF protein genes into human-human hybridomas and expressing them. Further, cell proliferation is enhanced by the expression of FGF proteins, whereby the amounts of biologically active substances are also increased. Accordingly, biologically active substances such as antibodies can be efficiently produced and recovered using serum-free media. This is particularly advantageous for industrial production.

Moreover, cloning in serum-free media becomes possible by introduction and expression of the FGF protein genes. This means that a single cell can be selected in a serum-free medium, which is very useful for an improvement in the reproduction of the hybridomas.

The present invention will hereinafter be described in more detail with the following examples. It is understood of course that these examples are not intended to limit the scope of the invention. Transfected human-human hybridoma HPO-75.29-H74 obtained in Example 2 described below was deposited with the Institute for Fermentation, Osaka, Japan (IFO), under the accession number IFO 50245 on May 8, 1990. This hybridoma cell line was deposited with the Fermentation Research Institute, the Agency of Industrial Science and Technology, the Ministry of International Trade and Industry, Japan (FRI), under the accession number FERM BP-2939 on Jun. 1, 1990 under the Budapest Treaty.

EXAMPLE 1 (1) Introduction of bFGF Gene into Human-Human Hybridoma

As a vector containing bFGF gene, pTB732 [R. Sasada et al., Mol. Cell. Biol, 8, 588-594 (1988)]was used. Antibody high-productive cell line HPO-75.29C derived from anti-HBsAg human MoAb-producing human-human hybridoma HBW-4.16 [K. Harada et al., Bio/Technoloqy 7, 374-377 (1989)]was suspended in a 0.3 M sucrose solution (sterility) at a density of $1 \times 10^7$ cells/ml. In 100 μl of the resulting suspension, 25 μg of plasmid pTB732 treated with restriction enzyme ClaI and 5 μg of plasmid pRSV$_{neo}$ [Science 221. 551 (1983)]treated with restriction enzyme BamHI were mixed. The resulting mixed solution was introduced into a centrifuge chamber of an electroporation device (DPE), and centrifuged at 2,000 rpm for 2 minutes. Then, the voltage of 1,000 V/3 mm was once applied thereto for 30 seconds, followed by standing for 10 minutes in ice water. The cells subjected to electroporation treatment were suspended at a density of $1 \times 10^5$ cells/ml in IsF medium containing antibiotic G418 (Sigma, U.S.A.) at a concentration of 1 mg/ml, and inoculated into each well of 96-well multiplate in an amount of 100 μl/well, followed by cultivation in a carbon dioxide incubator at 37° C. for 2 weeks. Then, 7 proliferated clone cell lines were selected.

(2) Detection of Introduced Gene

The cells ($1 \times 10^8$ cells) were suspended in 200 μl of 10 mM Tris-HCl buffer (pH 7.4), and the same amount of 0.4 M Tris-HCl buffer (pH 8.0), 100 mM EDTA, 1% SDS and 200 μg/ml proteinase K (BRL, U.S.A.) was added thereto, followed by heat treatment at 60° C. for 1 hour. The same amount of phenol-chloroform was added thereto to take a supernatant, and the same amount of chloroform was further added to take a supernatant again. To the resulting DNA solution, 0.1 part by volume of 3 M NaOH was added, and heat treatment at 60° C. was conducted for 1 hour, followed by cooling to room temperature. Then, the same amount of 2 M ammonium acetate was added thereto for neutralization. The solution was adsorbed by a nitrocellulose filter previously wetted with 1 M ammonium acetate by using a dot blotting device (Bio RAD), and dried at 80° C. for 2 hours.

In a separate reaction, plasmid pTB732 was treated with restriction enzymes EcoRI and PstI, and then subjected to agarose gel electrophoresis to cut out a bFGF-containing band. The band was purified by using Ultrafree C3HV (Millipore, U.S.A.), and labeled with $32_{P-dCTP}$ by random priming by using an Oligolabelling Kit (Pharmacia LKB Biotechnology, Sweden).

A nitrocellulose filter and a prehybridization solution [50% formamide, $5 \times$ SSC, $5 \times$ Denhardt's solution, 50 mM sodium phosphate buffer (pH 6.5), 250 ng/ml single stranded DNA]were placed in a plastic bag, and incubated at 42° C. for 8 hours. Then, the solution was exchanged for a hybridization solution [50% formamide, $5 \times$ SSC, $1 \times$ Denhardt's solution, 20 mM sodium phosphate buffer (pH 6.5), 10% dextran sulfate, 100 μg/ml single stranded DNA, heat-treated probe], followed by incubation at 42° C. for 15 hours. The filter was washed twice with $2 \times$ SSC and 0.1% SDS for 10 minutes, and then, further washed twice for 20 minutes with the same buffer heated at 68° C. After the filter was washed with $2 \times$ SSC twice, water was removed with filter paper, and the filter was subjected to autoradiography ($-70°$ C., 2 days).

Note: SSC (0.15 M NaCl, 15 mM sodium citrate (pH 7.0))

As the result of the autoradiography, human-human hybridomas HPO-75.29-N27, HPO-75.29-N58 and HPO-75.29-N73 were obtained which gave apparently strong autoradiograms compared to the control cells into which the plasmids were not introduced.

EXAMPLE 2

25 μg of plasmid pTB732 treated with restriction enzyme ClaI was mixed with 5 μg of plasmid p201 [J. L. Yates et al., Nature 313, 812-815 (1985)]treated with restriction enzyme BamHI, and both the plasmids were co-introduced into the human-human hybridoma HPO-75.29C cell line in the same manner as with Example 1 (1). As a selecting agent of a gene-introduced clone, 500 μg/ml of hygromycin (Behringer Manheim Yamanouchi) was used. The detection of the introduced gene was carried out in the same manner as with Example 1 (2). Consequently, as cell lines for which the introduction of bFGF gene was confirmed, human-human hybridomas HPO-75.29-H54 and HPO-75.29-H74 were obtained.

EXAMPLE 3

Each of the clones obtained in Examples 1 and 2 was inoculated into serum-free culture medium PEG-86-1 [Y. Shintani et al., Appl. Microbiol. Biotechnol. 27, 533-537 (1988)]at a density of about $1 \times 10^3$ cells/ml, and dispensed to a 24-well multiplate in an amount of 1 ml/well. Then, the culture was conducted without shaking in a 5% carbon dioxide incubator at 37° C. for 7 days and for 14 days. The number of the cells in the resulting culture broth was counted, and the results are shown in Table 1.

TABLE 1

| Comparison of Original Cell Lines and bFGF Gene-Introduced Cell Lines in Proliferated Amounts (Plate Cultivation) | | |
|---|---|---|
| | Cell number ($\times 10^3$/ml) | |
| Cell line | Cultivation for 7 days | Cultivation for 14 days |
| HPO-75.29C | 2.2 | 15 |
| HPO-75.29-N27 | 7.7 | 170 |
| HPO-75.29-N58 | 7.7 | 190 |
| HPO-75.29-N73 | 12.0 | 230 |
| HPO-75.29-H54 | 12.5 | 210 |
| HPO-75.29-H74 | 17.0 | 330 |

As can be seen from Table 1, the original Cell Line HPO-75.29C was low in proliferated amounts biginning with an inoculation of $1 \times 10^3$ cells/ml. However, for the bFGF gene-introduced cell lines, a significant enhancement in proliferation was observed.

EXAMPLE 4

Each of human-human hybridoma HPO-75.29-H74 (B) cell line (IFO 50245, FERM BP-2939) most proliferated in Example 3 and original cell line human-human hybridoma HPO-75.29C (A) was inoculated into serum-free medium PEG-86-1 at a density of about $1 \times 10^3$/ml, and an agitation culture was carried out at 37° C. for 15 days using 125-ml Techne spinner flasks. As a result, the results shown in FIG. 1 was obtained. Referring to FIG. 1, -●- indicates the total number of cells, -○- indicates the number of viable cells, and ▲ indicates the production amount (μg/ml) of anti-HBsAg human MoAb.

As apparent from FIG. 1, the bFGF gene-introduced cell lines remarkably increased in cell proliferation and antibody production, compared to the original cell line.

EXAMPLE 5

Each of human-human hybridoma HPO-75.29-H74 and the original cell line, human-human hybridoma HPO-75.29C, was inoculated into 100 μl of serum-free medium PEG-86-1 in each well of 96-well plastic plates so as to contain 0.5 cell/well, and incubated in a 5% carbon dioxide incubator at 37° C. for 15 days. For the original cell line HPO-75.29C, no cell proliferation was observed in all of the wells of the four 96-well plates, namely in 384 wells. For HPO-75.29-H74 cell line, cell proliferation was observed in 10 wells of 384 wells.

The following references, which are referred to for their disclosures at various points in this application, are incorporated herein by reference.

Nature 249, 123 (1974)
Proc. Natl. Acad. Sci. USA 82, 6507-6511 (1985)
The EMBO Journal 5, 2523-2528 (1986)
Biochem. Biophys. Res. Commun. 138, 611-617 (1986)
Endocrinology 97, 120 (1975)
J. Cell Biol. 70, 395 (1976)
J. Cell. Physiol. 91, 977 (1977)
Proc. Natl. Acad. Sci. U.S.A. 73, 4120 (1976)
J. Cell Biol. 66, 451 (1975)
Saibo Seicho Inshi (Growth Factors), page 32, edited by The Japanese Tissue Culture Association, Asakura Shoten, 1984
Cellular Immunology 122, 424 (1989)
Science 233, 545-548 (1986)
Science 233, 541-545 (1986)
PCT International Publication No. WO/87/01728
FEBS Letters 213, 189-194 (1987)
EP Publication No. 237,966 (Japanese Patent Unexamined Publication No. 63-226287/1988)
EP Publication No. 281,822 (Japanese Patent Unexamined Publication No. 2-193/1990)
Biochemical and Biophysical Research Communications 151, 701 (1988)
EP Publication No. 326,907
Biochem. Biophys. Res. Commun. 133, 554-562 (1985)
Mol. Cell. Biol. 4, 817 (1984)
J. Mol. App. Genet. 2, 101 (1983)
Cell 39, 653 (1984)
Cell 23, 175 (1981)
Proc. Natl. Acad. Sci., U.S.A. 78, 2072 (1981)
Methods in Enzymol. 101, 387 (1983)
Mol. Cell. Biol. 5, 410 (1985)
Cell. 37, 1053 (1984)
Nature 294, 228 (1981)
Ann. Rev. *Biochem.* 55, 913 (1986)
Mol. Cell. Biol. 3, 280-289 (1983)
Cell 22, 777-785 (1980)
Cell 32, 1105-1113 (1983)
Proc. Natl. Acad. Sci. U.S.A. 79, 6899-6902 (1982)
Nature 297, 205-208 (1982)
Japanese Patent Unexamined Publication No. 61-52293/1986
Cell 16, 777 (1979)
Hybridoma 4, 47 (1985)
Biochem. Biophys. Res. Commun. 129, 26 (1985)
Biochem. Biophys. Res. Commun. 142, 805 (1987)
Bio/Technology 7, 374-377 (1989)
Text for 2nd Symposium on Research and Development Project of Basic Technology for Future Industries-Biotechnology 1, 61 (1984)
J. Exp. Med. 147, 923 (1978)
Proc. Natl. Acad. Sci. 53, 288 (1965)
Amer. J. Hyg. 78, 173 (1963)
Japanese Patent Unexamined Publication No. 60-145088/1985
Mol. Cell. Biol, 8, 588-594 (1988)
Science 221, 551 (1983)
Appl. Microbiol. Biotechnol. 27, 533-537 (1988)

What is claimed is:

1. A hybridoma producing a monoclonal antibody and carrying an expression vector for aFGF, bFGF or a mutein thereof, said vector containing a DNA sequence coding for said aFGF, bFGF or mutein thereof.

2. A hybridoma in accordance with claim 1, in which said hybridoma is a human-human hybridoma.

3. Human-human hybridoma HPO-75.29-H74.

4. A method for producing a hybridoma producing a monoclonal antibody and carrying an expression vector for aFGF, bFGF or a mutein thereof, said vector containing a DNA sequence coding for said aFGF, bFGF or mutein thereof, which comprises transforming a hybridoma producing a monoclonal antibody with an expression vector for aFGF, bFGF or a mutein thereof, said vector containing a DNA sequence coding for said aFGF, bFGF or mutein thereof.

5. A method for producing a monoclonal antibody, which comprises i) cultivating a hybridoma producing a monoclonal antibody and carrying an expression vector for aFGF, bFGF or a mutein thereof, said vector containing a DNA sequence coding for said aFGF, bFGF or mutein thereof, in a culture medium, ii) producing aFGF, bFGF or a mutein thereof in a culture, iii) producing and accumulating a monoclonal antibody in the culture, and iv) recovering said monoclonal antibody.

6. A method in accordance with claim 5, in which said culture medium is a serum-free culture medium.

* * * * *